US011983308B2

(12) United States Patent
Jaeken et al.

(10) Patent No.: US 11,983,308 B2
(45) Date of Patent: May 14, 2024

(54) VIRTUAL REALITY INSTRUMENT FOR THE AUTOMATIC MEASUREMENT OF REFRACTION AND ABERRATIONS OF THE EYE

(71) Applicant: Bart Jan Jaeken, Murcia (ES)

(72) Inventors: Bart Jan Jaeken, Murcia (ES); Diego Ramon Garcia Sanchez, Elche (ES); Brian Vohnsen, Dublin (IE)

(73) Assignee: Bart Jan Jaeken, Murcia (ES)

( * ) Notice: Subject to any disclaimer, the term of this patent is extended or adjusted under 35 U.S.C. 154(b) by 661 days.

(21) Appl. No.: 15/734,977

(22) PCT Filed: Jun. 6, 2019

(86) PCT No.: PCT/IB2019/054708
§ 371 (c)(1),
(2) Date: Dec. 3, 2020

(87) PCT Pub. No.: WO2019/234670
PCT Pub. Date: Dec. 12, 2019

(65) Prior Publication Data
US 2021/0089118 A1      Mar. 25, 2021

(30) Foreign Application Priority Data
Jun. 8, 2018   (ES) .............................. ES201830558

(51) Int. Cl.
*G06F 3/01* (2006.01)
*A61B 3/00* (2006.01)
*A61B 3/028* (2006.01)
*A61B 3/103* (2006.01)
*G02B 27/01* (2006.01)
*G02B 27/16* (2006.01)

(52) U.S. Cl.
CPC ............ *G06F 3/013* (2013.01); *A61B 3/0008* (2013.01); *A61B 3/028* (2013.01); *A61B 3/103* (2013.01); *G02B 27/017* (2013.01); *G02B 27/16* (2013.01)

(58) Field of Classification Search
CPC ....... G06F 3/013; A61B 3/0008; A61B 3/028; A61B 3/103; G02B 27/017; G02B 27/16
USPC ......................................... 351/205–206, 246
See application file for complete search history.

(56) References Cited

U.S. PATENT DOCUMENTS 9,167,965 B2 * 10/2015 Jaeken ................... A61B 3/103
2008/0018855 A1 * 1/2008 Larichev ................ A61B 3/032
600/558

(Continued)

FOREIGN PATENT DOCUMENTS

WO       2016/149416 A1      9/2016

*Primary Examiner* — James R Greece
(74) *Attorney, Agent, or Firm* — Maschoff Brennan

(57) ABSTRACT

A virtual reality instrument measures the refraction and aberrations of the eye in an automatic way, and includes a portable part which is a virtual reality headset foreseen of a detailed screen per eye and at least one background screen, both virtual. The detailed screen has a resolution multiple times the foveal resolution of the eye and the background screen has the resolution similar to the peripheral resolution of the eye. The virtual reality instrument also includes at least one pupil camera, a system to manipulate the phase of the light coming from the detailed screen, a wavefront sensor and light source to measure the wavefront using a wavelength of at least 400 nm.

17 Claims, 3 Drawing Sheets

(56) References Cited

U.S. PATENT DOCUMENTS

2012/0287398 A1* 11/2012 Baker .................. A61B 3/103
                                                    351/201
2017/0323485 A1   11/2017 Samec

* cited by examiner

VIRTUAL REALITY INSTRUMENT FOR THE AUTOMATIC MEASUREMENT OF REFRACTION AND ABERRATIONS OF THE EYE

SECTOR OF THE TECHNOLOGY

The invention belongs to the field of optics, specifically medical devices which can measure refractive error and aberrations of both eyes.

The device is a tool to measure the refractive error and the visual performance of humans. The information obtained with the device can be used the prescribe vision aids to correct the refractive error. Further, the device can be used to evaluate the progression of several vision parameters and control the visual performance.

BACKGROUND OF THE INVENTION

In Europe, more than half of the population needs some kind of visual aid to see well and this percentage is growing due to various causes. One is the aging of the population, but another important factor is the upcoming myopia epidemic. Investigation has shown that in several areas in Asia more than 90% of the people in specific age groups are myopic ('The Myopia Boom', E. Dolgin, Nature 519, 276-278; 2015). During the span of life almost everybody undergoes a vision test either to determine the required correction for their myopia, hyperopia or presbyopia, or to test their visual performance.

Currently the gold standard to measure the refractive error of humans is a two-step protocol. In the first step and ophthalmologist or optometrist takes an objective measurement. Typically, an autorefractor or retinoscopy is used. The result obtained from this measurement is used as a starting point of the subjective refinement. In this second step, the subject is looking to a fixation target through possible corrections. The operator changes the optical correction in function of the answers the subject gives to several questions like, 'which solution do you like best' or 'can you read the letters'. In general, a phoropter is used but also a trial frame with trial lenses can be used. The fixation target is often a test showing optotypes of different sizes representing different visual acuities. For example, the ETDRS (Early Treatment Diabetic Retinopathy Study) is often used. These methods have been in use for more than 100 years, and in this century the methodology has changed very little. This is mainly because up to now the results of the subjective refinement are still clinically significant different from the results obtained with the objective measuring devices. For many years, specialists have been debating the efficiency and the precision of the current two-step measurement procedure. Clinical studies have shown that the repeatability is poor: >±0.5 D. This imprecision has a significant impact on the quality of life of the people and the society in general. It generates accidents, reduces the productivity, increases the possibility of getting depressed and can cause delays in the development of children.

The patent application US 2012/0287398 A1 describes an instrument that analyzes the binocular vision to determine the power of the visual aids. The instrument contains a first and a second target, one for each eye of the subject and at least one light source to illuminate those targets. It consists of optics which makes virtual images of the first and the second target. A beam splitter is in front of the first and the second eye guides the virtual images towards the eyes. The instrument also includes components to correct sphere and cylinder. They suggest an external target can be used. This target can be any element which generates enough contrast with respect to the virtual target ensuring that this virtual target can be seen clearly. The external target can be placed on a wall, on a table or fixed to the device. When near vision tests are performed, the target can be mounted on an inclined rail respecting the conversion of the eyes.

This configuration can consist of various problems which will have impact on the precision of the result. On one hand, systems with an open field of view try to replicate the natural viewing conditions. But very often they suffer from unstable test condition. The background light intensities and the distances to the background target are difficult to control properly. This is avoided by making the background dark enough to ensure it doesn't disturb the virtual test, but in that cause the advantages of having an instrument with an open field of view are lost.

The use of a rail, which is adjusted for each subject and test, is little practical and increases strongly the amount of error on the result.

In case of doing far vision tests while the external fixation target is fixed to the device and the target is not completely dark, additional optics is required to ensure the target is optically at infinity to avoid influencing the optical properties of the subject.

Finally, when background targets are used, as mentioned in the patent application US2012/0287398, which are not entirely black, a decrease of contrast of the virtual target will be caused.

SUMMARY OF THE INVENTION

The object of the presented invention is a device which solves the above-mentioned problems. The instrument can be used to measure the refractive error of a subject, measuring the ocular aberrations of both eyes while the subject receives different visual stimuli of virtual tests. The virtual test is an assembly of a background, created by a background screen, and a center, created with a high-resolution screen. The first generates a large field of view of uniform light adjustable in intensity and color. A dark mask is present where the detailed screen overlaps the background screen. The detailed target can control de optotype and its dynamics, the intensity, contrast and color. The resolution is multiple times the foveal resolution. This makes it possible to test visual acuity in small steps over a large dynamic range. The assemble creates a virtual environment which in size and resolution equals an open field of view, but easily controlled. The positioning of the fixation target is controlled by the optics through which the subject is looking at the target. Using variable optics, the position of the target can be controlled fast and with high precision. Having an entirely virtual test environment makes it possible to fully control the ambient light conditioning, ensuring that the test conditions are exactly as needed and fully independent of the light conditions of the measuring room. The presence of two screens, one background screen and one detailed screen, make it possible to create a large field of view, to make it immersive, and generate 'natural' viewing conditions similar or better than a device with an open field of view.

In addition, between the subject eyes and the detailed fixation target, adaptive optics is present. In this way it is possible to vary this optics while observing the behavior of the eye provoked by these changes. To determine the behavior of the eye the aberrations are measured, the gaze direction, the pupil size, and the blinking frequency. A1 measurements are done in real time at high frequency, at least 10

Hz. The results of the conducted measurements and the characteristics of the subject are analyzed in real time to get to the final result. The result, together with all relevant data of the measurement session are stored in a database in that way that it can be used to improve the measurement process in the future. The system is binocular and has two optical paths, one for each eye. The control of those paths can be done independently. It can be used monocular when only one of the paths is active or binocular when both are active.

In contradiction to the conventional systems, the present invention is much smaller in size and weight. It consists of a portable part (a VR headset which is worn by the subject), a control system like a tablet or a mobile phone and a unit the power the two components and can be used to calibrate the headset. The virtual reality instrument to measure the refraction and the aberrations of the eye in an automated way consists of: an external fixed part with a programmable controller and a portable part which look like a VR headset where the headset consists of a whole of optical components creating two optical paths, one for each eye. In addition, it had a fixation system consisting of one detailed screen for each eye and at least one background screen. Both are virtual. The detailed screen has a resolution many times the foveal resolution of the eye and the background screen has a resolution similar to the resolution of the human peripheral vision. It also has an optical relay subsystem which generates at least two conjugated planes of the pupil of the subject for each eye. One plane to measure and one to manipulate the phase of the light of the detailed screen. Also, components which can manipulate the phase of the light are present. Even as, components to vary to position of the two optical paths in an independent way with respect to the pupils of the subject along the horizontal and the vertical axis which are perpendicular with respect to each other and the optical axis of the optical subsystem and optionally with respect to the nodal point of the eye aligned to headset. The headset has also at least one pupil camera and a set of associated diodes to illuminate each eye in order to make it possible to see the pupil with the pupil camera. At least one laser source is present or an adapted diode to send the light into the eye and of which the reflected light is captured and used to determine the refraction and the aberrations of the eye.

Other beneficial properties are summarized in continuation and in the claims.

BRIEF SUMMARY OF THE FIGURES

With the objective to better understand the characteristics of the invention and to complete the description figures are included. Their purpose is the illustrate possible concepts, but it is not limited to these concepts.

DETAILED DESCRIPTION

Figure 1:
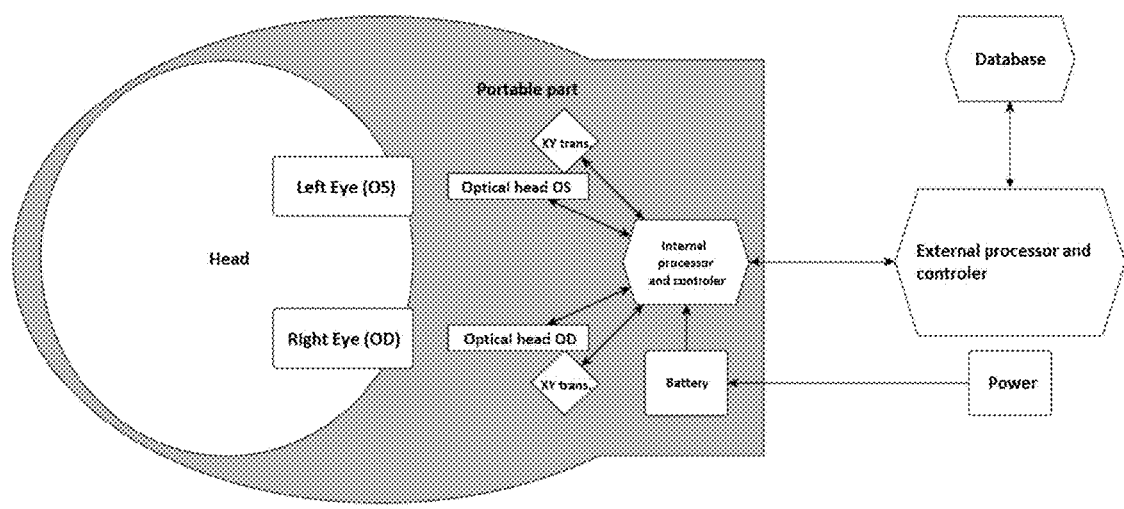
FIG. 1 shows a schematic of the mobile part and the control system of the invention.

The instrument consists of a portable part (VR headset) and an external controller like a tablet or a mobile phone. Also, it can be foreseen of a stage to power the two previously mentioned parts and to calibrate it. The headset consists of two optical heads, one for each eye (see FIG. 1). In general, the design of the two optical parts is symmetric. In some configurations de optical components and electro-optics are shared between both eyes. The optical path can be translated along the X-axis (left-right) and the Y-axis (up-down) with respect to the eyes in such a way as shown in the transversal cross-section in which the right eye is looked from above. The translations can be done independently between the eyes. This gives the opportunity to adjust the different optical axes with respect to the gaze direction of each eye independent. The translations can be done manually or motorized and can be controlled by an operator or by a gaze tracking algorithm. The instrument can be used to perform a multitude of measurements like the refraction, aberrations, pupil behavior, visual acuity, contrast sensitivity, defocus curve, corneal topography, or other vision tests. The data are stored in a server which can be in the cloud.

To measure the refraction and the aberrations objectively, a light source, typically a laser or a diode with a wavelength of at least 400 nm, and a wavefront sensor positioned in the pupil plane of the eye are present.

An adaptive or variable optics system (for example a badal system, a variable focal length lens, a set of cross-cylinders, a deformable mirror, a liquid crystal or phase plates) is placed in a conjugated plane (in one or multiple conjugated planes) with the pupil plane making it possible to manipulate the optics. One or multiple optical relay systems create one or multiple conjugated planes of the pupil plane. The optical paths, one each eye, make it possible to measure the aberrations and manipulate the phase of the light of the detailed fixation target at which the subject is looking.

The fixation target consists of a detailed screen and a background screen. The first has a resolution many times that of foveal vision making it possible to test visual acuity. The background screen has a low resolution similar to that of the peripheral vision. The detailed screen covers between 5 and 10 degrees while the background screen has a field of up to 60 degrees. The instrument is equipped with at least one pupil camera to determine the size of the pupil, the pupillary distance and the gaze direction. The translation system makes it possible to change the position of the two optical paths independently with respect to the pupils of the subject. The manipulation should be possible at least along the horizontal and vertical axis. The two axes are perpendicular to the optical axis of the optical paths. The three axes form a cartesian coordinate grid per eye creating a horizontal, sagittal, and frontal plane which are orthogonal with respect to each other. Optionally, the manipulation can be rotative around the nodal point of the eye which coincided with the exit pupil of the optical heads. The exit pupil is a frontal plane perpendicular to the optical axis of the optical head.

Integrated in the same device there is electronics which control and process the data. This system is responsible for the control of the mobile parts as well as the processing of the images and the coordination of the different tests. It consists of the control element, like a micro-controller or any kind of FPGA (field programmable gate array) or micro-processor, which can in real time and easy process the images and other acquired data like the communication from the externa controller which is the user interface.

Figure 2:
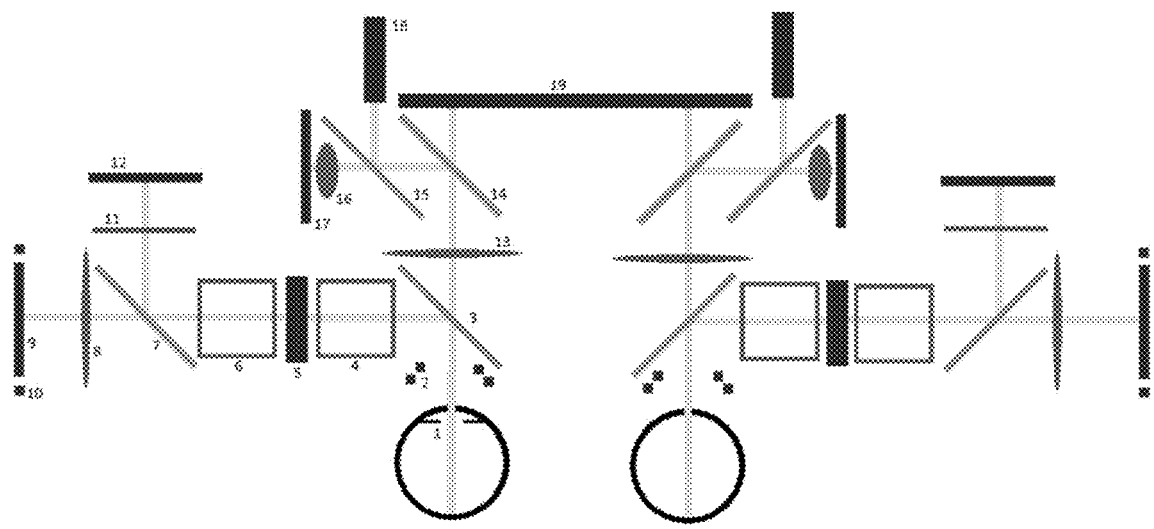
FIGS. 2-5 are schematics of possible embodiments of the invention which include different elements to change the optical path and change certain components (like the pupil camera) to obtain specific measurements.

FIG. 2 shows a schematic drawing of a possible optical configuration of the headset. The schematics are in two dimensions, but the device part of the invention could be in more planes and have bends which are not presence in order to fit into a small space. With respect to the figure, the pupil plane (exit plane) 1 is the plane of interest to manipulate and to measure the optics. When the headset is correctly aligned there are three conjugated planes with the pupil plane: 5, 8 and 11. The planes are obtained by using relay optics 4 and 6. The planes 5 and 8 can be used to manipulate the phase of the light coming from the detailed fixation target 9. The manipulation of the phase can be done with a set of lenses, variable focus length lenses, phase plates, deformable mirrors or liquid crystal (as for example LCoS). Plane 11 contains a microlens array used to sample the wavefront in this plane based on the Hartmann-Shack principle, although also other types of aberrometers can be used. In this setup, the largest part of the light with a ratio of 30/70 (30% transmission and 70% reflection) is reflected on the beam splitter 3. The beam splitter 7 can be optics which reflects a specific band of the light spectrum similar to the wavelength of the light source 18, while transmitting the rest of the spectrum.

Lens 8 is a collimating lens which sends the image created by the micro-screen 9 to infinity. This micro-screen 9 is a high resolution (full HD or larger) MOLED which generates the detailed fixation target. Also, LCD screens can be used. It is important that the image has high resolution to be able to sample the visual acuity is small steps around visual acuity 0 expressed in LogMar. Here, small steps are referred to steps of 0.05 to 0.1 LogMar. The screen will have a size of 5 to 10 degrees of visual angle which coincides with the foveal vision of the subject. Other requirements of this screen are the control of the luminance, contrast, color and dynamics.

Around the screen there is a group of LEDs 10 which can be controlled independent from the screen. The LEDs can vary in intensity and color.

The opto-electrical CMOS or CCD sensor 12 is part of the wavefront sensor. Sensor 12 has to be very sensitive, especially in the near infrared (NIR) range since this is mostly used for performing the wavefront measurements in plane 11. A collimating lens 13 with large numerical aperture sends the light of the background screen 19 to infinity. The resolution requirement of this screen is lower than that of the screen 9 and should be similar to that of the peripheral vision. The visual field is much larger (up to 60 degrees) compared to the detailed screen 9. It should be possible to control the intensity and the color. The configuration shown in FIG. 2 has a shared background screen 19 between the two optical heads and is fixed to the frame of the headset. This makes it independent from the manipulation of the position of the optical heads. This background screen 19 will have a part which is used for the right eye and a part which is used for the left eye. In function of the pupillary distance of the subject, different parts of the screen will be vignetted to ensure that the detailed screen is always in the center of the complete image (detailed image+background image). The complete image is the combination of the image of the detailed screen and the background screen where, to avoid loss of contrast, the overlapping part is blacked on the background screen. The position of this area varies as a function of the alignment of the optical heads. Additionally, the test (detailed screen and part of the background screen) can be turned on or off eye independent: only right eye, only left eye, or both eyes.

The beam splitters 14 and 15 can be bandpass filters. In case of beam splitter 14 it is possible to use a beam splitter which divides the visible light and the NIR. In the case of beam splitter 15 it is possible to select a specific one in function of the wavelength of the measurement laser 18 and the wavelength of the LEDs 2 which illuminate the eye. These LEDs can be in a plane or in the shape of a cup in front of the eye to illuminate the eye or to generate concentric patterns. The measurement wavelength should be outside the visible spectrum or being a short pulse because it is important that the subject can't see the light to avoid the contraction of the pupil of the subject. A possible spectrum range can be between 400 and 980 nm. It is also important that the LED's which illuminate the eye are from wavelength outside the visible range to avoid the contraction of the subject's pupil. Finally, a set of lenses 16 project the image of the eye on the active part (CMOS or CCD) of the sensor 17.

The components 2, 5, 9, 10, 12, 17, 18 and 19 are connected to an internal processor/controller which is connected by cable or wireless to the external controller which serves as interface between the operator and the headset and between the operator and the database. In addition, it can be used to process part of the acquired data. From here, the operator starts the different protocols to perform the vision testing of the subject or to consult historic data.

Figure 3:
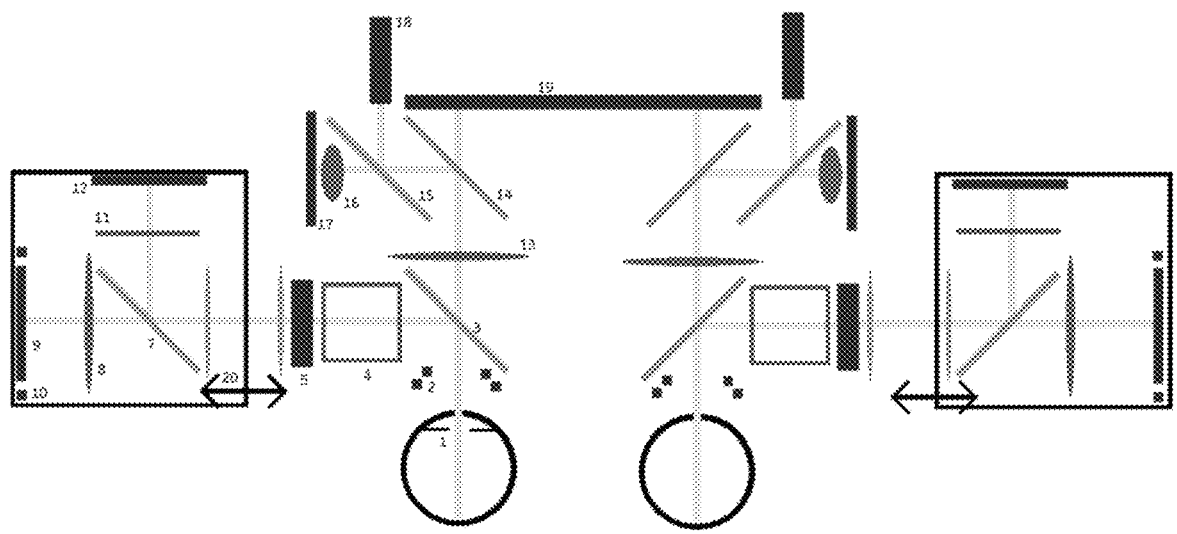

A second embodiment (FIG. 3) includes a badal system (20) to change the defocus compensation. In this configuration plane 5 stays accessible to manipulate the cylinder and manipulate other aberrations. The part 20 of the optical head is moved along the optical path to compensate in this way the defocus through with the subject looks at the detailed test.

Figure 4:
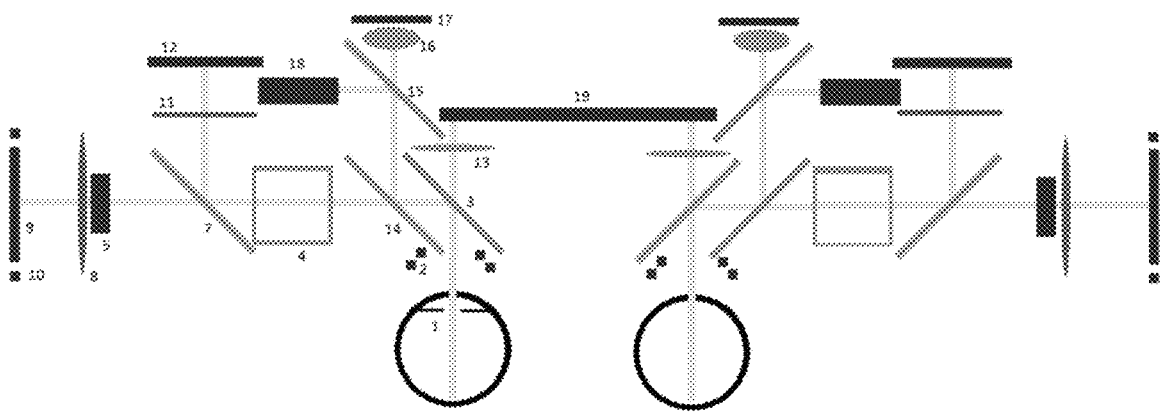

Another embodiment (FIG. 4) allows a reduction from 3 to 2 conjugated planes per eye. In this way there is only one plane to manipulate the optics and on plane to measure the aberrations. The advantages are that configuration reduces the number of components and miniaturizes the whole. A disadvantage is that the wavefront sensor must have a large dynamic range.

Figure 5:
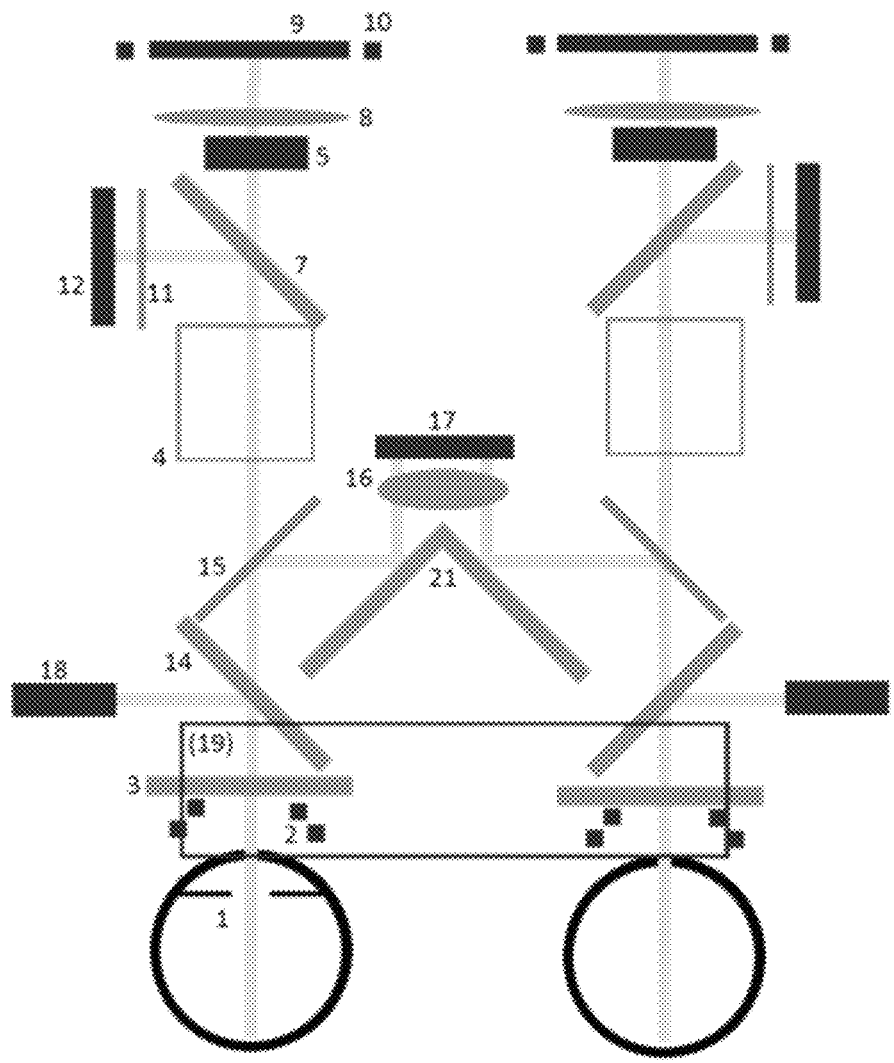

Another embodiment is shown in FIG. 5 in which the pupil camera is shared. The camera (or set of cameras) take the image of eyes in direct vision. It consists of an opto-electronic part like a CMOS or CCD 17 and an optical part 16 to focus and optionally filter the light using a small bandpass filter adjusted to the wavelength of the illumination LEDs 2. The beam splitter 3 in front of the eye or eyes, transmits in this specific case, 70% of the light and reflects 30%, sending part of the light to a collimating lens with large numerical aperture 13 and the background screen 19 which is shared by both eyes. The light transmitted by the beam slitter 3 goes to another beam splitter 15 but of another type (10% transmission and 90% reflection). The relay optics 4 consists in this specific configuration of two different groups of lenses creating a conjugated pupil plane for measuring the aberrations and the conjugated pupil plane to manipulate the optics through which the subject is looking at the detailed test. The sets of lenses can have different focal lengths to adjust the magnification according to the application. For example, the set of lenses to create the plane for measuring the aberrations can cause a minification while to other set of lenses to create the optics manipulation plane can have a magnification of one. By dividing the two optical paths, a cold mirror 7 (can also be a hot mirror if the two paths are interchanged) transmits the measurements light when this light is in the near infrared spectrum and reflects the visible light spectrum.

The advantages are the reduction of the number of components and the miniaturization. In contrary, the disadvantage is that the wavefront sensor needs to have a larger dynamic range.

The processing/controlling unit consists of different subsystems:
  An interface to control and exchange of data with at least 3 screens and up to six cameras
  Electronic subsystem to control the internal mechanics Electronic subsystem to control de variable lenses or to manipulate electro-optics electronically Electronic subsystem to control the movements of the cylindrical lenses to vary the cylinder Subsystem to control the LED array Communication subsystem connected to an external control element either by cable or wireless The foreseen system could consist of a combination of FPGA, micro-processors, and micro-controllers. The FPGA subsystem is responsible for the acquisition and the processing of the signals coming from the CMOS sensors (cameras), as well as the control of the different screens. By making those processes independent from the micro-processor a higher acquisition speed can be obtained which enables parallel working between the different elements. In some cases, as in the measurement system and the eye tracking, the images are first processed by integrated systems (SoC System on chip) which send the data directly to the FPGA subsystem to reduce the processing time and the final consumption and reduce the heat dissipation. The micro-controller subsystem is in charge of the management of the different actuators using the correct ICs. In the same way as with the acquisition the micro-controller system allows to control different elements in real time.

Finally, there is the components based on a micro-processor which coordinates the different subsystems, allows external control and connects with the cloud-based systems. It can be a Linux based system which runs the main control application, and which offers a user-friendly interface which allows in an easy way to configure and maintain the instrument. The obtained results together with the relevant data are registered in a data base. The processing of those data is done using artificial intelligence giving the operator relevant information of improving his decision making. The algorithm is continuously improved by automatic training.

The instrument contains different guided protocols. Guided protocols are series of actions which the operator follows to get to a specific end point. In addition to providing a guided protocol to measure the refractive error, also a fully automated mode is present. This procedure consists of three phases:

Phase 1: An objective measurement is performed in an iterative process of measuring the aberrations of the eye in real time and overcompensating (adding 0.5 D mor refraction) the refraction with the adaptive optics system. When the difference in the measured refraction between step x and step x+1 is smaller than 0.25 D the process is considered the have stabilized. The found refraction is used as input for the next phase.

Phase 2: Consists of a series of scans, varying gradually the optics through which the subject looks at the detailed test, while registering and analyzing the ocular behavior metrics: aberrations, pupil size, direction of gazing and blinking frequency. The scans and the fixation target vary in function of the results of the analyzis of the ocular behavior, the characteristics of the subject and the user case objective of the measurement. When the probability is below a defined threshold, for example 3σ, the second eye is measured. In case the both eyes have been measured, phase 3 will start.

The characterization of the subject and the interpretation of the results of the measurements determine the next vision test that will be performed. The process is continuously optimized using the results of the analyzis of big data. All devices are connected to a central server where the results of the measurements are collected to continuously improve the algorithm.

While phase 1 and 2 are monocular (only one eye is stimulated at the time), phase 3 is a binocular validation. Both eyes are stimulated. The refractions found at the end of phase 2 are placed as correction in the adaptive optics. The behavior of both eyes is analyzed in the same way as in phase 2 but now with both eyes stimulated. The data of phases 2 and 3 generate a map of the dynamic range of the visual system of the subject. Together with the data of the subject and the objective of use, the optimal refraction is determined.

A specialist in the field can understand that presented description and figures are just possible embodiments of the invention but that multiple variations can be made to those embodiments without exceeding the objective of the invention as claimed.

The invention claimed is:

1. A virtual reality instrument for measuring the refraction and aberrations of the eye in an automated way, comprising:
   an external fixed part with a controller and options to program; and
   a portable part, including a virtual reality headset having:
      a set of optical elements which make two optical paths, one for each eye;
      a fixation target including a detailed screen per eye and at least one background screen, both virtual, wherein:
         the detailed screen has a resolution multiple times that of the foveal vision and the background screen has a resolution similar to that of the peripheral vision of the eye;
      an optical relay subsystem that generates at least two conjugated planes with the pupil of the subject for each eye, a measurement plane and a plane to manipulate the phase of the light coming from the detailed screen components to manipulate that phase of the light components that vary the position of the two optical paths in an independent way with respect to the position of the pupils of the subject at least in the horizontal and the vertical axis which are perpendicular between each other and perpendicular with the optical axis of the optical subsystems and optionally also with respect to the nodal point of the eye aligned in the headset;
      at least one pupil camera and a set of associated diodes to illuminate each eye so that the pupil camera is capable to detect the pupil at least on wavefront sensor per eye to measure the refraction and the aberrations of the eye in an objective way; and
      a laser light source or diode adapted to send light into each eye in the way that the reflected light can be used to determine the refraction and aberrations of the eye.

2. The virtual reality headset of claim 1, further comprising:
   two components to vary the position of the optical paths in a manual or motorized way.

3. The virtual reality headset of claim 2, further comprising:
   programmable components to control the variation of the optical paths by means of eye tracking algorithms.

4. The virtual reality headset of claim 1, wherein:
   the detailed screen covers between 5 and 10 degrees of the visual field; and
   the at least one background screen covers a visual field of up to 60 degrees.

5. The virtual reality headset of claim 1, further comprising:

a badal system in each optical path which can vary defocus.

6. The virtual reality headset of claim 1, further comprising:
in each optical path, a set of cylindrical lenses in a rotation stage to compensate astigmatism.

7. The virtual reality headset of claim 1, further comprising:
in each optical path, at least one opto-electrical lens with variable focal length in function the change of current, used to compensate defocus.

8. The virtual reality headset of claim 1, further comprising:
in each optical path, at least one opto-electrical system, including a liquid crystal (LCoS) or a deformable mirror, to compensate the refraction or the aberrations.

9. The virtual reality headset of claim 1, wherein:
a light source is used to measure the wavefront, which can be pulsed and in the visible or the infrared spectrum.

10. The virtual reality headset of claim 1, wherein:
the controller has programmable components to vary the content of the screens, change the variable optics, measure the refraction and aberrations with a frequency of at least 10 Hz, measure the pupil size, the blinking frequency and the gaze direction with a frequency of at least 10 Hz and process the acquired data in real time to determine the measurement flow and calculate the optimal refraction.

11. A method for measuring aberrations and the refraction of an eye of a subject, comprising:
measuring the eye of the subject using the virtual reality headset of claim 1, while varying the optics of the virtual reality headset.

12. The virtual reality headset of claim 2, wherein:
the detailed screen covers between 5 and 10 degrees of the visual field; and
the at least one background screen covers a visual field of up to 60 degrees.

13. The virtual reality headset of claim 2, further comprising:
a badal system in each optical path which can vary defocus.

14. The virtual reality headset of claim 2, further comprising:
in each optical path, a set of cylindrical lenses in a rotation stage to compensate astigmatism.

15. The virtual reality headset of claim 3, wherein:
the detailed screen covers between 5 and 10 degrees of the visual field; and
the at least one background screen covers a visual field of up to 60 degrees.

16. The virtual reality headset of claim 3, further comprising:
a badal system in each optical path which can vary defocus.

17. The virtual reality headset of claim 3, further comprising:
in each optical path, a set of cylindrical lenses in a rotation stage to compensate astigmatism.

* * * * *